United States Patent [19]

Naffziger

[11] 4,388,297

[45] Jun. 14, 1983

[54] STABLE TOCICANT COMPOSITIONS OF CHLORPYRIFOS

[75] Inventor: David H. Naffziger, Midland, Mich.

[73] Assignee: The Dow Chemical Company, Midland, Mich.

[21] Appl. No.: 258,099

[22] Filed: Apr. 27, 1981

Related U.S. Application Data

[63] Continuation-in-part of Ser. No. 161,101, Jun. 19, 1980, abandoned.

[51] Int. Cl.$^3$ ............... A61K 31/74; A01N 57/00; A01N 57/26; A01N 27/00
[52] U.S. Cl. ..................... 424/78; 424/200; 424/365
[58] Field of Search ............ 424/200, 78, 193, 365

[56] References Cited

U.S. PATENT DOCUMENTS

| 2,564,606 | 8/1951 | Percy et al. | 424/189 |
| 2,664,381 | 12/1953 | Omohundro et al. | 424/189 |
| 3,185,562 | 5/1965 | Scoles et al. | 424/192 |
| 3,683,078 | 8/1972 | Haus | 424/193 |

FOREIGN PATENT DOCUMENTS 1054049  5/1979  Canada .
1551829  9/1979  United Kingdom .

OTHER PUBLICATIONS

McCutcheon's–Detergents & Emulsifiers–1973 Ed. pp. 171–172, note T–Det C–40.
Chem. Abst. 72, 47,366(a) (1970)–Mendenwald.
Chem. Abst. 85, 138,644z (1976)–Stenger et al.
The Merck Index, 9th ed.(1976)–item 2179.

*Primary Examiner*—Douglas W. Robinson

[57] ABSTRACT

Stable toxicant compositions comprising a toxicant and a Castor Oil based nonionic surfactant containing from about 5 to about 55 moles of ethylene oxide chemically combined with each mole of Castor Oil.

8 Claims, No Drawings

STABLE TOCICANT COMPOSITIONS OF CHLORPYRIFOS

CROSS REFERENCE TO RELATED APPLICATION

This application is a continuation-in-part of copending application Ser. No. 161,101 filed June 19, 1980, now abandoned.

BACKGROUND OF THE INVENTION

This invention relates to stable toxicant compositions.

As aromatic solvent prices increase and supplies become increasingly restricted the demand for toxicant formulations based on water is increasing. Hitherto such compositions have commonly been stable at either high or low temperatures, but not at both.

DESCRIPTION OF THE PRIOR ART

U.S. Pat. No. 3,683,078, issued Aug. 8, 1972, describes and claims transparent toxicant compositions containing alkyl phenol/alkylene oxide condensation products.

British Pat. No. 1,551,829 published Sept. 5, 1979 describes a process for the preparation of aqueous dispersions wherein the mixture is subjected to a grinding operation such that the mean particle size of the solid is reduced to below 20 microns.

SUMMARY OF THE INVENTION

This invention provides a stable toxicant composition which is in the form of a solution which is dispersible in water to form a stable emulsion and which comprises the following components: (A) at least one insecticidally active toxicant, (B) at least one nonionic surfactant comprising a Castor Oil based nonionic surfactant and (C) at least one anionic surfactant; the proportions of said components being such that the composition is dispersible in water to form a stable emulsion which is insecticidally active. The composition of this invention may be prepared by combining the components in any order or manner and stirring the mixture, with heating if desired, until a homogeneous stable solution is formed. The flash point of such mixtures is generally and preferably above 100° F.

Stable aqueous emulsions are prepared by diluting the compositions with water to prepare the desired final concentration of toxicant. In such dilutions the toxicant may be present in amounts of from about 0.001 to about 10 percent by weight, advantageously about 0.006 to about 10 percent by weight and preferably from about 0.01 to about 5 percent by weight. Additives such as antifoamers, reodorants, antimicrobials and the like may be added if desired.

The compositions of this invention can be frozen and thawed without destabilizing. Further, the compositions can be heated to 50° C. without destabilizing and they can be stored for at least six months at room temperature without destabilizing.

DETAILED DESCRIPTION OF THE INVENTION

Water immiscible solvents, i.e., solvents that are insoluble in water or only slightly soluble in water, such as, for example, hydrocarbon and chlorinated hydrocarbon solvents may be employed in amounts of from 0 to about 75 percent by weight, based on total composition weight, to provide low temperature stability and, when used, are preferably used in an amount of from about 2 to about 50 percent by weight. Aromatic hydrocarbon solvents such as, for example, the isomers of triethylbenzene, ethylmethylbenzene, xylene, toluene, and ethylnaphthalenes are preferred, although other water immiscible solvents known to those skilled in the art may be employed. Mixtures of the above may also be utilized.

Anionic surfactants which are soluble in the toxicant-solvent-surfactant solution such as, for example, the alkali or alkaline earth metal salts of dodecylbenzenesulfonic acid, are employed in amounts of from about 5 to about 50 percent by weight, preferably in amounts of from about 5 to about 30 percent by weight, based on the total weight of the concentrate.

In addition to the Castor Oil based nonionic surfactant, which is critical to the present invention, and is advantageously employed in amounts of from about 10 to about 80 percent by weight, preferably in amounts of from about 20 to about 60 percent by weight, based on the total weight of the concentrate, one may employ other nonionic surfactants such as, for example, the alkylphenol/alkylene oxide condensation products taught in U.S. Pat. No. 3,683,078 and the products obtained by reacting propylene glycol with propylene oxide followed by ethylene oxide to molecular weight of about 2,000 to about 3,000 or more.

The Castor Oil based nonionic surfactant preferably contains from about 5 to about 55 moles of ethylene oxide chemically combined with each mole of Castor Oil and advantageously contains from about 30 to about 50 moles of ethylene oxide per mole of Castor Oil.

The stable toxicant compositions of this invention advantageously comprise from about 1 to about 50 percent by weight, based on total composition, of the toxicant which is, preferably, pyrethrin, a synthetic pyrethroid, a thiophosphate ester or a carbamic acid ester.

When employing a solvent the toxicant/solvent ratio may be from about 10:1 to about 1:10 on a weight basis. The preferred ratio is from about 10:1 to about 2:1.

The synthetic pyrethroids which may be employed in the present invention include, for example, those having the formula

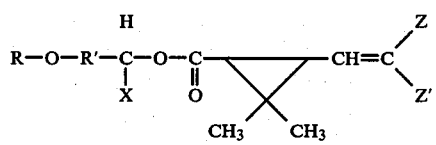

wherein R and R' are interchangeably phenyl, pyridyl or substituted phenyl or pyridyl rings, X is hydrogen or cyano and Z and Z' may be the same or different and each is halo such as chloro, bromo or fluoro. Preferred pyrethroids are permethrin, decamethrin, dimethrin and cypremethrin.

Thiophosphate esters which may be employed in the present invention include, for example, coumophos, bromophos-ethyl, diazinon, dioxathion, chlorpyrifos, ethion, malathion, oxinothiophos, benoxaphos, carbophenothion and phosmet which are described in The Wellcome Foundation Ltd.'s South African Patent Application 77/7609. The preferred thiophosphate esters are chlorpyrifos and chlorpyrifos-methyl.

Carbamic acid esters which may be employed in the present invention include, for example, those described in U.S. Pat. Nos. 3,111,539; 3,062,864; 3,062,865;

3,062,866; 3,062,867; 3,062,868; 2,903,478; 3,336,186 and 2,681,879. Propoxur, carbaryl and carbofuran are preferred carbamic acid esters.

By "insecticidally active" is meant that the toxicants are adapted to kill or control insects when applied to the habitats thereof by means generally employed by those skilled in the art.

The following examples, wherein all percentages are by weight unless otherwise indicated, further illustrate the present invention.

EXAMPLE 1

| Chlorpyrifos | 30 |
|---|---|
| Tenneco ® 500/100 | 20 |
| Casul ® 70HF | 18 |
| T-Det ® N - 10.5 | 12 |
| T-Det ® C-40 | 20 |

Tenneco ® 500/100 is a mixture of isomers of triethylbenzene, ethylmethylbenzene and o-xylene.

Casul ® 70HF is the calcium salt of dodecylbenzenesulfonic acid.

T-Det ® N-10.5 is the reaction product of nonylphenol with about 10 moles of ethylene oxide.

T-Det ® C-40 is the reaction product of one mole of Castor Oil with 40 moles of ethylene oxide.

The ingredients were combined and stirred at 50° C. for about one-half hour forming a homogeneous stable composition. Dilution of 1.7 parts of this composition with 98.3 parts water followed by mild agitation provided a stable emulsion suitable for use.

Employing the above procedure the following formulations were prepared, in each case forming a stable composition and a stable emulsion when diluted.

EXAMPLE 2

| Chlorpyrifos | 30 |
|---|---|
| Tenneco ® 500/100 | 20 |
| Casul ® 70HF | 15 |
| T-Det ® C-40 | 35 |

EXAMPLE 3

| Chlorpyrifos | 30 |
|---|---|
| Tenneco ® 500/100 | 20 |
| Casul ® 70HF | 12 |
| T-Det ® EPO - 61 | 8 |
| T-Det ® C-40 | 30 |

T-Det ® EPO-61 is the reaction product of propylene glycol with propylene oxide and then ethylene oxide to a molecular weight of about 2000.

EXAMPLE 4

| Diazinon | 19.3 |
|---|---|
| 40% Pyrethrin Conc. | 4.8 |
| Piperonyl Butoxide | 5.8 |
| Tenneco ® 500/100 | 20.0 |
| Casul ® 70HF | 18.0 |
| T-Det ® N - 10.5 | 12.0 |
| T-Det ® C-40 | 20.0 |

Dilution of 5.2 parts of this composition with 94.8 parts water followed by mild agitation produced a stable emulsion suitable for use.

The addition of 3.3 percent by weight of the α-cyano-3-phenoxybenzyl ester of 3-(2,2-dichloroethenyl)-2,2-dimethylcyclopropane carboxylic acid to 96.7 percent by weight of the mixture of Example 3 resulted in the formation of a stable composition and a stable emulsion when diluted.

The addition of 7 percent by weight of resmethrin to 93 percent by weight of the mixture of Example 3 also resulted in the formation of a stable composition and a stable emulsion when diluted.

The substitution of diazinon (87.9%) for chlorpyrifos in Examples 1 and 3 resulted in the formation of stable compositions and stable emulsions on dilution.

The substitution of chlorpyrifos-methyl for chlorpyrifos in Example 3 resulted in the formation of a stable composition and a stable emulsion on dilution.

The substitution of malathion for chlorpyrifos in Example 1 resulted in the formation of a stable composition and a stable emulsion on dilution.

The following formulations also provided compositions in solution form which were dispersible in water to form stable emulsions.

EXAMPLE 5

| Chlorpyrifos | 25 |
|---|---|
| Tenneco ® 500/100 | 10 |
| Anionic* | 5 |
| T-Det ® N - 10.5 | 20 |
| T-Det ® C-40 | 40 |

*Diethanolamine salt of dodecylbenzenesulfonic acid.

EXAMPLE 6

| Chlorpyrifos | 40 |
|---|---|
| Tenneco ® 500/100 | 4 |
| Anionic* | 8 |
| T-Det ® EPO-61 | 20 |
| T-Det ® C-40 | 28 |

See Example 5

EXAMPLE 7

| Chlorpyrifos | 25 |
|---|---|
| Tenneco ® 500/100 | 15 |
| Anionic* | 5 |
| T-Det ® EPO-61 | 17 |
| T-Det ® C-40 | 38 |

*Ninate 415—K salt of an aryl alkyl sulfonic acid.

EXAMPLE 8

| Propoxur | 5 |
|---|---|
| Ethyl acetate | 45 |
| Anionic* | 10 |
| T-Det ® EPO-61 | 15 |
| T-Det ® C-40 | 25 |

*See Example 5

What is claimed is:

1. A stable insecticidally active composition which is in the form of a solution which is dispersible in water to form a stable emulsion and which comprises the following components: (A) from about 1 to about 50 percent by weight of total composition of chlorpyrifos, (B) from about 10 to about 80 percent by weight of total composition of a Castor Oil based nonionic surfactant containing from about 5 to about 55 moles of ethylene oxide chemically combined with each mole of Castor Oil and (C) from about 5 to about 50 percent by weight of total composition of an anionic surfactant.

2. Composition of claim 1 which comprises, in addition, from 0 to about 75 percent by weight of a water immiscible solvent.

3. Composition of claim 2 wherein the toxicant-solvent ratio is from 10:1 to 1:10.

4. Composition of claim 1 which comprises from 5 to 30 percent by weight of an anionic surfactant.

5. Composition of claim 1 which comprises, in addition, from 0 to 40 percent by weight of a non-Castor Oil based nonionic surfactant.

6. Composition of claim 1 which has been diluted with water to contain from 0.001 to 10 percent by weight toxicant.

7. Composition of claim 1 wherein the Castor Oil based nonionic surfactant is present in an amount of from about 20 to about 60 percent by weight, based on the total weight of the concentrate.

8. Composition of claim 1 wherein the Castor Oil based nonionic surfactant contains from about 30 to about 50 moles of ethylene oxide per mole of Castor Oil.

* * * * *

UNITED STATES PATENT AND TRADEMARK OFFICE
CERTIFICATE OF CORRECTION

PATENT NO. : 4,388,297
DATED : June 14, 1983
INVENTOR(S) : David H. Naffziger

It is certified that error appears in the above—identified patent and that said Letters Patent is hereby corrected as shown below:

Cover page, first column, in the title, "TOCICANT" should read --TOXICANT--.

Column 1, line 1, "TOCICANT" should read --TOXICANT--; line 53, "reodorants" should read --deodorants--.

Signed and Sealed this

Twenty-fifth Day of October 1983

[SEAL]

Attest:

GERALD J. MOSSINGHOFF

Attesting Officer

Commissioner of Patents and Trademarks